US012773401B2

(12) United States Patent
Rajendran et al.

(10) Patent No.: US 12,773,401 B2
(45) Date of Patent: Oct. 27, 2026

(54) PHARMACEUTICAL COMPOSITIONS OF OVATODIOLIDE AND THE USE THEREOF

(71) Applicant: Anison Therapeutics Oy, Turku (FI)

(72) Inventors: Senthil Kumar Rajendran, Åbo (FI); Preethy Paul, Åbo (FI); Yury Brusentsev, Åbo (FI); Patrik Eklund, Åbo (FI); John Eriksson, Åbo (FI); Maria Sippola-Thiele, Chapel Hill, NC (US)

(73) Assignee: Anison Therapeutics Oy, Turku (FI)

( * ) Notice: Subject to any disclaimer, the term of this patent is extended or adjusted under 35 U.S.C. 154(b) by 1067 days.

(21) Appl. No.: 17/619,637

(22) PCT Filed: Jun. 16, 2020

(86) PCT No.: PCT/FI2020/050429
§ 371 (c)(1),
(2) Date: Dec. 16, 2021

(87) PCT Pub. No.: WO2020/254726
PCT Pub. Date: Dec. 24, 2020

(65) Prior Publication Data

US 2022/0296565 A1 Sep. 22, 2022

(30) Foreign Application Priority Data

Jun. 17, 2019 (FI) ..................................... 20195527

(51) Int. Cl.

| | |
|---|---|
| ***A61K 31/365*** | (2006.01) |
| ***A61K 9/06*** | (2006.01) |
| ***A61K 9/107*** | (2006.01) |
| ***A61K 36/00*** | (2006.01) |
| ***A61P 17/12*** | (2006.01) |
| ***A61P 31/12*** | (2006.01) |
| ***A61P 35/00*** | (2006.01) |

(52) U.S. Cl.
CPC .............. *A61K 31/365* (2013.01); *A61K 9/06* (2013.01); *A61K 9/107* (2013.01); *A61P 17/12* (2018.01); *A61P 31/12* (2018.01); *A61P 35/00* (2018.01); *A61K 36/00* (2013.01)

(58) Field of Classification Search
CPC ........ A61K 31/365; A61K 9/06; A61K 9/107; A61K 36/00; A61P 35/00; A61P 31/12; A61P 17/12
See application file for complete search history.

(56) References Cited

U.S. PATENT DOCUMENTS 8,969,410 B1 3/2015 Shih et al.

FOREIGN PATENT DOCUMENTS

| | | | |
|---|---|---|---|
| CN | 104072513 | A | 10/2014 |
| CN | 104869991 | A | 8/2015 |
| TW | 201225970 | A | 7/2012 |
| WO | WO20140333366 | A1 | 3/2014 |
| WO | WO2016027005 | A1 | 2/2016 |

OTHER PUBLICATIONS

Alam (Fitoterapia 71 2000 574-576) (Year: 2000).*
Marshall (Tetrahedron Letters, Vo1.27, No. 40, pp. 4873-4876, 1986) (Year: 1986).*
Lin (Phytomedicine 46 (2018) 93-103) (Year: 2018).*
Yang (Biomedicine & Pharmacotherapy 103 (2018) 118-126) (Year: 2018).*
Akbarsha et al: Antiproliferative property of n-hexane and chloroform extracts of Anisomeles malabarica (L). R. Br. in HPV16-positive human cervical cancer cells. Journal of Pharmacology and Pharmacotherapeutics, Jan. 1, 2012, vol. 3, 9 pages.
Arisawa et al: Biological active macrocyclic diterpenoids from chinese drug "Fáng Féng Cáo"; II. Derivatives of ovatodiolids and their cytotoxity. Planta Medica, Thieme Verlag, Aug. 1, 1986, No. 4, pp. 297-299.
Arisawa et al: Biologically Active Macrocyclic Diterpenoids from Chinese Drug "Fáng Féng Cáo" I. Isolation and Structure. Planta Medica, 1986, vol. 3, No. 1, pp. 38-41.
Hsieh et al: Inhibition of pro-inflammatory mediators and tumor cell proliferation by Anisomeles indica extracts. Journal of Ethnopharmacology, Jun. 19, 2008, vol. 118, No. 1, pp. 65-70.
Jarrett et al: High incidence area of cattle cancer with a possible interaction between an environmental carcinogen and a papilloma virus. Nature, Jul. 20, 1978, vol. 274, pp. 215-217.
Liu et al: Ovatodiolide suppresses nasopharyngeal cancer by targeting stem cell-like population, inducing apoptosis, inhibiting EMT and dysregulating JAK/STAT signaling pathway. Phytomedicine, 2018, vol. 56, pp. 269-278.
Preethy et al: Analysis of the Cytotoxic Potential of Anisomelic Acid Isolated from Anisomeles malabarica. Scientia Paharmaceutica, Jan. 25, 2013, vol. 81, pp. 559-566.
Preethy et al: Antiproliferative property of n-hexane and chloroform extracts of Anisomeles malabarica (L). R. Br. in HPV16-positive human cervical cancer cells. Journal of Pharmacology and Pharmacotherapeutics, Jan. 1, 2012, vol. 3, No. 1, pp. 26-34.
Scudellari: "Sex, Cancer and a Virus". Nature, Nov. 21, 2013, vol. 503, No. 7476, pp. 330-332.
Zur Hausen: Condyloma acuminata and human genital cancer. Cancer Research, Feb. 1978, vol. 36, No. 794, p. 794.

* cited by examiner

*Primary Examiner* — Kortney L. Klinkel
*Assistant Examiner* — Richard Grant Peckham
(74) *Attorney, Agent, or Firm* — Laine IP Oy; Mark W. Scott

(57) ABSTRACT

A pharmaceutical composition for anti-viral treatment for papillomavirus associated diseases in mammals, comprising a therapeutically effective amount of Ovatodiolide or Ovatodiolide related substances or an enriched plant extract containing anisomelic acid and ovatiodiolide. The pharmaceutical composition may comprise Ovatodiolide or Ovatodiolide related substances or the enriched extract in an oil-in-water emulsion, for example in an isotropic mixture of at least one oil and at least one surfactant or, alternatively, in a hydrophilic solvent and a co-solvent or surfactant or a combination thereof. A method of treating or preventing papillomavirus associated diseases in a mammal is also provided.

18 Claims, 9 Drawing Sheets

Before treatment After treatment

| **Animal number** | **Dose (mg/ kg) of refined extract** | **Body weight (g)** | | | |
|---|---|---|---|---|---|
| | | Day 0 | Day 7 | Day 14 | Weight gain (g) |
| **1** | 300 mg/ kg | 219,5 | 248,9 | 267,9 | 48,4 |
| **2** | 2000 mg/ kg | 205,6 | 225,5 | 242,0 | 36,4 |
| **3** | 2000 mg/ kg | 201,4 | 227,8 | 243,7 | 42,3 |
| **4** | 2000 mg/ kg | 207,9 | 235,4 | 242,6 | 34,7 |
| **5** | 2000 mg/ kg | 199,9 | 232,1 | 233,0 | 33,1 |
| **6** | 2000 mg/ kg | 208,2 | 244,0 | 258,7 | 50.5 |

PHARMACEUTICAL COMPOSITIONS OF OVATODIOLIDE AND THE USE THEREOF

BACKGROUND OF THE INVENTION

Field of the Invention

The present invention relates to a novel use of a compound, Ovatodiolide isolated from *Anisomeles malabarica/Anisomeles indica/Anisomeles ovata*, and the refined extract (containing anisomelic acid and ovatodiolide) from *A. malabarica* and/or *A. indica*. In particular, the present invention concerns pharmaceutical compositions of Ovatodiolide. The present invention also discloses the use of Ovatodiolide and the refined extract and compositions thereof in treatment of the papillomavirus associated diseases. The invention also relates to refined/enriched extracts of *Anisomeles malabarica* and/or *Anisomeles indica* and/or *Anisomeles ovata*, the extracts comprising Ovatodiolide and Anisomelic acid, or related substances, for use in the treatment of papillomavirus associated diseases, and to a process for the preparation of the enriched extracts with or without any formulations.

Background

Human papillomavirus (HPV) infection is now a well-established cause of different types of cancer including but not limited to cervical cancer. There is also growing evidence of HPV being a relevant factor in head and neck cancers and other epithelial cancers (anogenital).

Most HPV cancers are caused by infection with a range of high-risk 'oncogenic' human papillomavirus (HPV) types. Moreover, it is now accepted that more than 70% of head and neck cancer in the USA and 99% of cervical cancer worldwide is initiated by HPV infection.

Papillomaviruses induce a variety of lesions both in humans and in animals. Some papillomas, albeit benign, are themselves a clinical problem, such as laryngeal papillomas of children or penile papillomas of bulls, and others are known to be a risk factor in the pathogenesis of cancer, as in the case of flat lesions of the cervix or penile condylomata in humans (zur Hausen, 1978) and papillomas of the alimentary canal in cattle (Jarrett et al, 1978). In particular, human papillomavirus types HPV-16 and HPV-18 and bovine papillomavirus type 4 are potentially carcinogenic. Therefore, both in human and veterinary medicine an antiviral drug would be of major importance.

Integration of the HPV viral genome and expression of E6 and E7 viral proteins are critical steps in the development of HPV-mediated cancers. Elimination of the trophic sentinel response by E6 protein occurs through several important mechanisms. The best-characterized mechanism involves the inactivation and degradation of the tumor suppressor p53. E6 undermines the tumor suppressor function of p53 through the formation of a complex with a cellular protein called E6-associated protein (E6-AP). As a result, the G1/S and G2/M cell cycle checkpoints are lost, and the cell is susceptible to genomic instability that may allow for the development of neoplasia.

The current standard therapy for head and neck cancer is a combination of cisplatin a toxic, potent chemotherapy drug and radiation. This has many potential side effects, including damage to the voice box and throat, which can hinder the ability to speak and swallow. With the younger, healthier HPV-positive patients, who are 58% less likely to die within three years of treatment than HPV-negative patients, clinicians worry about the long-term effects of the treatment and are exploring techniques including less-toxic chemotherapy regimens.

In the continuing search for agents that may treat or ameliorate the affliction of cancer, natural products have provided an endless supply of active compounds that are increasingly being exploited. Several plant-derived compounds are currently successfully employed in cancer treatment.

Ovatodiolide is a diterpenoid isolated from *Anisomeles malabarica* (L.) R. Br., a herb belonging to the family Labiatae. Ovatodiolide is also available in other *Anisomeles* species such as *Anisomeles indica* and *Anisomeles ovata*. In general, all these anisomeles plant species are recommended in ancient medicines for use in catarrh, intermittent fever, bowel disorder, and cancer. Previously, the use of an anisomelic acid isolated from *Anisomeles malabarica* in anti-HPV cancer therapy has been suggested (WO 2014/033366 A1).

So far, Ovatodiolide as such or as an extract comprising Ovatodiolide and Anisomelic acid has not been suggested or used for the treatment of papillomavirus associated diseases.

SUMMARY OF THE INVENTION

The present invention is based on the finding that Ovatodiolide exhibits good efficiency in inducing apoptosis in HPV positive cervical cancer cells and cytotoxicity in HPV-positive head and neck patient-derived cancer cells.

Surprisingly it has been found that Ovatodiolide inhibits protein level expression of E6 and E7, and thus is capable of acting as an anti-HPV agent.

Results obtained in connection with the present invention reveal OVT as a compound with a novel mechanism of action that restores growth arrest and induces apoptosis in HPV positive cells.

Surprisingly, the potency of Ovatodiolide or "OVT" in inducing apoptosis in cervical cancer cells is considerably higher than that of Anisomelic acid (AA). OVT was found to be more effective than AA in inducing caspase-3 activation which is a hallmark of programmed cell death (apoptosis). OVT also enhances the activity of AA while at the same time primary cells are not killed, the combination thus exhibiting both enhanced activity and specificity towards cancer cells. Thus, a combination of OVT and AA provides additional advantages in inducing apoptosis in HPV positive cancer cells.

It has now also been found that extraction of *Anisomeles malabarica* and *Anisomeles indica* plant materials, particularly aqueous alcoholic or ether extraction, provides extracts that effectively reduce cell viability of HPV positive cervical cancer cells. The extracts which comprise a combination of Ovatodiolide or Ovatodiolide related substances and Anisomelic acid, isomers and salts thereof ("AA"), particularly extracts in enriched and preferably purified form, are useful for the treatment of papillomavirus associated diseases. Surprisingly, it has also been found that the enriched or refined extracts, which comprise a combination of OVT and AA, can be used without further purification in a product for treatment of Papillomavirus mediated warts in mammals, including humans and animals.

To the inventor's knowledge, this is the first disclosure of OVT as an inhibitor of viral oncoprotein expression and as a chemotherapeutic agent for Papillomavirus (PV)-induced diseases that includes papillomavirus associated non-cancerous lesions, like warts seen in humans and animals. Due to the general importance of the role of E6/E7 oncoproteins in papilloma mediated cancers diseases, said compound and derivatives thereof can be used more broadly in the treatment of papillomavirus mediated diseases.

Based on these findings, the present invention provides for pharmaceutical compositions of OVT, for example in the form of extracts, in particular plant extracts, for use in-papilloma virus mediated diseases that includes non-cancerous lesions, like warts in mammals, including humans and animals.

Furthermore, the present invention provides for compositions of OVT in the form of emulsions or precursors thereof, in particular, oil-in-water based microemulsions or precursors thereof.

The present invention also provides for the use of OVT, for example in the form of emulsions, optionally formed in vivo, in anti-viral cancer therapy and for an improved method of anti-viral cancer therapy comprising the steps of administering to a mammal an efficient amount of Ovatodiolide or Ovatodiolide related substances.

The present invention further provides for the use of OVT and OVT compositions, for examples extracts, in particular plant extracts, preferably formulated in the form of emulsions, in anti-viral cancer therapy and for an improved method of anti-viral cancer therapy comprising the steps of administering to a mammal an efficient amount of Ovatodiolide and Ovatodiolide related substances.

The present invention also provides for a method of treating benign or neoplastic genital Papillomavirus associated diseases, in particular, Papillomavirus mediated genital warts, as well as non-genital warts, comprising the step of administering to an animal a therapeutically effective amount of Ovatodiolide.

The present invention also provides enriched extracts of *Anisomeles malabarica, A. indica, A. ovata*, or a combination thereof, particularly enriched extracts of *Anisomeles malabarica/Anisomeles indica*, comprising Ovatodiolide or Ovatodiolide related substances and Anisomelic acid and related substances (AA). The invention also provides pharmaceutical compositions comprising said enriched extracts, the use of said extracts in the treatment of papillomavirus associated diseases, and a process for the preparation of said enriched extracts.

The invention is defined by the features of the independent claims. More specifically, the pharmaceutical compositions for use in the treatment of papillomavirus associated diseases according to the present invention are mainly characterized by what is stated in the characterizing part of claim 1. Some specific embodiments are defined in the dependent claims.

A mammal includes both human and non-human mammals. A non-human mammal includes, without limitation, ungulates, such as bovine or equine, particularly even-toed ungulates, such as bovine, preferably cattle, but also other non-human mammals, for example rabbits, or rodents such as hamsters, mice and companion animals such as dogs, cats etc.

Considerable advantages are obtained by means of the present invention.

The present invention discloses that Ovatodiolide, already as such, is an efficient inhibitor of HPV16-E6 and E7 oncoproteins expressed in cervical cancers. Ovatodiolide induces both cell cycle arrest and apoptosis in cervical cancer cells, which will enable its use as a drug to arrest cancer cell proliferation and also to kill cancer cells. The commercial use of Ovatodiolide can further be broadened to treat other papillomavirus related infections such as skin warts and genital warts.

The apoptosis induction exhibited by Ovatodiolide is surprisingly more efficient than by Anisomelic acid. In fact, OVT is much more active at small dosages compared to AA, while also specific at lower doses.

In one embodiment, OVT is used in the form of an emulsion, preferably a microemulsion, for example in the form of a fine oil-in-water microemulsion. The solubility and delivery of OVT can be improved by preparing the pharmaceutical composition in the form of an emulsion or in the form of a mixture which forms an emulsion upon administration or in vivo, thus increasing the therapeutic usage of the compound.

In a further embodiment, OVT is used in the form of a pharmaceutical composition comprising Ovatodiolide and Anisomelic acid. Since OVT enhances the activity of AA and AA has more specificity than OVT, the combination of OVT and AA exhibits both enhanced activity and specificity towards cancer cells.

In an embodiment, the pharmaceutical composition comprises an enriched extract comprising Ovatodiolide or Ovatodiolide related substances and AA. The enriched extracts are prepared by a selective process, which gives extracts containing higher amounts of active compounds than prior known methods, thus enabling the enriched extract to be used without further purification for example in products for treatment of Papillomavirus mediated warts.

Next, the novel technology will be examined more closely with the aid of a detailed description with reference to the attached drawings.

BRIEF DESCRIPTION OF THE DRAWINGS

FIG. 4 also shows the downregulation of cIAP2 protein level and the cleavage of procaspase 3 (p37) by OVT treatment, indicating that the decrease in cell viability is a result of specific induction of apoptosis (programmed cell death).

DETAILED DESCRIPTION OF PREFERRED EMBODIMENTS

Figure 1A:
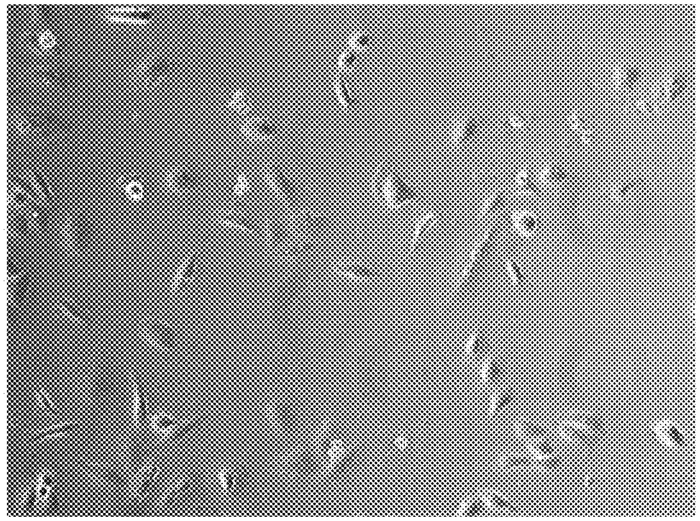
FIG. 1 shows the representative phase contrast microscopy images of untreated SiHa cells (FIG. 1A) and 40 μm Ovatodiolide (FIG. 1B) treated cells at 72 h time point. 40 μm treatment of OVT for 72 hours has a clear effect on cell morphology. OVT treated cells exhibit similar characteristics to apoptotic cells.

As discussed above, the present invention is based on the finding that Ovatodiolide is efficient in down-regulating viral oncoproteins E6 and E7, leading to apoptosis.

In particular, OVT exhibits good efficiency in inducing apoptosis in HPV16 positive cervical cancer cells at 20 and 40 μM. Thus, OVT induces apoptosis at a considerably lower dose than AA, making OVT a potent candidate for anti-viral cancer treatment.

Within the scope of the present invention, the abbreviation "OVT" stands for Ovatodiolide. Ovatodiolide has the general formula I.

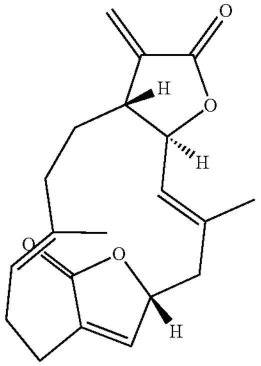

Its CAS number is 3484-37-5 and molecular formula $C_{20}H_{24}O_4$.

Included in the concept and covered wherever appropriate by the abbreviation "OVT" are also Ovatodiolide related substances such as pharmaceutically acceptable salts thereof, isoovatodiolide, 4-5-epoxovatodiolide, 4-hydroxy-5-enovatodiolide, 4-methylene-5-hydroxyovatodiolide, 4-methylene-5-oxovatodiolide and any derivatives which have a similar activity. Racemates, as well as optical isomers of Ovatodiolide and its derivatives, are also included herein.

In one preferred embodiment, "OVT" represents Ovatodiolide.

As used herein, the term "pharmaceutically acceptable salts" refers to salts or zwitterionic forms of Ovatodiolide. Salts of the Ovatodiolide can be prepared for example during isolation and purification of the acid or separately by reacting the acid with a compound having a suitable cation. Suitable pharmaceutically acceptable cations include alkali metal (e.g., sodium or potassium) and alkaline earth metal (e.g., calcium or magnesium) cations and ammonia cations. For some purposes of the present technology, OVT, in particular Ovatodiolide, is used in essentially pure form, i.e. at a purity of at least 70%, preferably at least 75%, more preferably at least 85%, advantageously at least 95%, suitably at least 98% and in particular at least 99.5%, or even 99.95%, by weight (of the active ingredient of the pharmaceutical composition). However, for certain purposes of the present technology, such as for treatment of warts, raw or enriched extracts of *A. malabarica/A. indica*, which comprise Ovatodiolide or Ovatodiolide related substances and Anisomelic acid, can be used even without further purification.

OVT can be obtained by extraction of natural raw materials containing said compound or it can be used as a synthetic compound. Some alternative ways of providing OVT will be discussed below.

As used herein, "OVT containing raw-material" is used for designating plant material which contains OVT (Ovatodiolide and Ovatodiolide related substances). The plant material typically comprises leaves, stems, flowers, roots and combinations thereof. Leaves are particularly preferred. The plants are exemplified by plants, in particular herbaceous plants, belonging to the *Anisomeles* genus, such as *A. malabarica, A. indica* and *A. ovata* and combinations thereof.

As used herein, the abbreviation "AA" designates Anisomelic acid and related compounds and substances, such as salts and isomers of Anisomelic acid.

The plant material can be fresh but preferably the plant material is used in dry or dried form. In particular, the moisture content of the plant material is less than 60 wt %, for example less than 50 wt %, such as less than 40 wt %, typically less than 30 wt % or less than 20 wt % or less than 10 wt %.

OVT can be obtained by methods per se, for example by isolation from *A. malabarica, A. indica* or *A. ovata*. Thus, in one embodiment, the method described by Arisawa et al., 1986 can be employed: The whole plant was shade-dried, powdered and extracted with 90% methanol in a soxhlet apparatus, then vacuum-dried. The methanolic crude extract was partitioned between chloroform and water. The chloroform layer was concentrated and partitioned between 90% methanol and petroleum ether. The 90% methanolic extract was concentrated and subjected to silica gel column chromatography which will yield different compounds and one of them is ovatodiolide.

Instead of methanol, ethanol can be used.

OVT can be co-extracted with AA (Anisomelic acid and related substances) from *A. malabarica* and/or *Anisomeles indica*. However, OVT is present in considerably higher quantities than AA in the raw plant material. The same extraction protocol may yield up to 5 times more OVT than AA. This high yield of OVT represents a considerable advantage, taking into account that also the apoptosis induction exhibited by OVT is more efficient than that exhibited by AA.

OVT can also be co-extracted with AA (Anisomelic acid and related substances) from an OVT containing raw-material, such as *A. malabarica, A. indica* or *A. ovata*, to obtain an extract comprising both OVT and AA, typically at weight ratios of 10:2.5 to 10:20 and a concentration of OVT and AA or more than 15 wt %.

In an embodiment, an OVT containing raw-materials, such as *A. malabarica* and/or *A. indica* plant material, is extracted with an alcohol, for example an aqueous alcoholic solvent, preferably with isopropanol or an aqueous solution thereof, or with ether, preferably methyl tert-butyl ether (MTBE). This extraction provides a raw extract with a yield of 5 to 15%, typically approximately 10% of the plant material. In an embodiment, this raw extract which typically has a combined concentration of AA and OVT of approximately 20%, is used as such, particularly for the treatment of warts.

The obtained extract may also be filtrated and preferably concentrated to dryness to obtain a residue extract. In an embodiment, the residue extract is dissolved in a solvent, such as an organic solvent, and if necessary filtrated.

The filtrate is preferably concentrated to dryness and the residue dissolved in an organic solvent, such as an aqueous alcoholic solvent. After washing the solution and optional further concentration, an enriched extract comprising OVT and AA is obtained.

In a further embodiment, *A. malabarica* and/or *A. indica* plant material is extracted with an alcoholic solvent, preferably isopropanol or an aqueous solution thereof, or with ether, such as methyl tert-butyl ether (MTBE), and the obtained extract is filtrated before treatment with activated charcoal or activated carbon. After removing the solvent and the activated carbon, an extract is obtained, which after optional washing and optional further concentration provides an enriched extract comprising OVT and AA.

In another embodiment, the extraction of *A. malabarica* and/or *A. indica* plant material with isopropanol of an aqueous solvent thereof, or with ether, such as methyl tert-butyl ether (MTBE), is performed in the presence of activated charcoal or activated carbon. After removing the solvent and the activated carbon, an extract is obtained, which after washing and optional further concentration provides an enriched extract comprising OVT and AA.

In one preferred embodiment, the extraction of *Anisomeles* plant material comprises the steps of extracting *Anisomeles* plant material, preferably leaves of *A. malabarica* and/or *A. indica*, with an alcoholic or ether solvent, preferably isopropanol or methyl tert-butyl ether, adding activated carbon, filtering the obtained mixture, and concentrating the extract, preferably to dryness to obtain a residue extract.

In the present context, the term "enrich" or "refine" stands for increasing the content of the compounds (OVT and/or OVT related substances and Anisomelic acid and related substances) over that of raw extract, i.e. an extract obtained directly of the natural material (e.g. plant material). The extract can be enriched with regard to at least one of, preferably all of the OVT and/or OVT related substances and Anisomelic acid and related substances typically with up to 15% or even 20% by weight or more. Thus, the concentration of OVT and/or OVT related substances and Anisomelic acid and related substances in the enriched extract is 1.1 to 25-fold by weight compared to that of an extract obtained directly from the natural material.

In one embodiment, the concentration of each of OVT and/or OVT related substances and Anisomelic acid and related substances is at least 50% (by weight) and up to 500% greater than in the extract obtained directly from the natural material.

OVT treatment leads to efficient apoptosis in HPV-positive cervical cancer cells and HPV-positive patient-derived head and neck cancer cells.

To the best of the inventors' knowledge, this is the first report to provide direct experimental evidence of the molecular mechanism behind OVT-induced apoptosis in HPV positive cancer cells. The results, thus, provide new insights into the possible molecular mechanisms of ovatodiolide, in addition to its new use as an anti-papillomavirus agent.

The present invention provides for therapeutic applications which comprise OVT, in particular, OVT in isolated, in isolated and purified form, or in the form of an enriched plant extract comprising OVT and AA, for the treatment of papillomavirus mediated disease.

Ovatodiolide is a hydrophobic compound which dissolves in DMSO and ethanol and is mostly insoluble in water. Hence, for successful delivery of drugs both orally and also by other means it is advantageous to improve the solubility.

The present invention provides for various approaches for this purpose like solid dispersion, anti-solvent, complexation with cyclodextrin and lipid-based formulations. There are various lipid-based emulsion delivery systems and one of them is self-microemulsifying drug delivery systems (SMEDDS). SMEDDS is defined as isotropic mixtures of natural or synthetic oils, solid or liquid surfactants, or alternatively, one or more hydrophilic solvents and co-solvents/surfactants that have a unique ability of forming fine oil-in-water (o/w) micro emulsions upon mild agitation followed by dilution in aqueous media, such as gastrointestinal (GI) fluids. SMEDDS spreads readily in the GI tract, and in some cases the digestive motility of the stomach and the intestine may provide agitation which achieves self-emulsification.

The SMEDDS mixture can be filled in either soft or hard gelatin capsules. A SMEDDS formulation according to the present invention comprises oils, surfactants and if required antioxidants. Co-surfactants and co-solvents can be added to improve the formulation characteristics.

Thus, in one embodiment, OVT, in particular Ovatodiolide, is dissolved in a hot ethanol to form a mixture and the mixture is dissolved in a surfactant or in a mixture of a surfactant, poly(ethylene glycol) and an oil. The ratio between the liquid components can vary between 1 part by weight of the alcohol to 100 parts by weight of the mixture formed by the surfactant, PEG and oil to 100 parts by weight of the alcohol to 1 part by weight of the mixture. Preferably the ratio is about 1 part of alcohol to 5 parts by weight of mixture—5 parts by weight of alcohol to 1 part by weight of mixture, for example about 1-2 parts by weight to 0.5 to 1 part by weight of the components in the earlier indicated order.

In view of the chemical properties of the compound, as OVT is a diterpenoid, like paclitaxel, a well-known anti-tumor agent, OVT can be administered topically, parenterally, intraperitoneally or intravenously. OVT emulsions can be administered orally.

The active components are used in effective amounts. The route of administration, the dosage as well as the exact formulation are chosen depending on the subject's condition. Thus, the interval can be adjusted individually to provide levels of the active compound in the blood plasma that are sufficient to maintain and obtain the desired therapeutic effects. In general, however, doses employed for humans typically are in the range of 0.001 mg/kg to about 1000 mg/kg per day, in a range of about 0.1 mg/kg to about 500 mg/kg per dose of inhibitor. Typically, OVT is administered at 0.001 to 100 mg/kg body weight, for example at 0.01 to 50 mg/kg body weight. In some embodiments, OVT can be employed in doses ranging from about 0.1 to about 50 mg/kg, about 0.5 to about 40 mg/kg or about 0.7 to about 30 mg/kg. Specific doses contemplated include sub-ranges of any of the foregoing ranges in 0.1 mg/kg increments. Due to its high potency, OVT can be administered at lower doses compared to AA.

The pharmaceutical composition will comprise OVT either as the primary or as the sole therapeutically efficient component (or agent). Therefore, within the scope of the present technology, compositions are also provided wherein the effective agent consists of or consist essentially of ovatodiolide, ovatodiolide related substances and salts thereof. Naturally, it is possible to combine OVT with other anticarcinogenic compounds, such as tyrosine kinase inhibitors, such as Pazopanib, and angiogenetic agents, such as vascular endothelial growth factor inhibitors, e.g. Bevacizumab. In one embodiment, the pharmaceutical composition will thus comprise a combination of OVT with an approved cancer therapeutic.

In a further embodiment the pharmaceutical composition will comprise a therapeutically effective amount of Anisomelic acid or salts thereof, in addition to Ovatodiolide or Ovatodiolide related substances. The weight ratio of OVT and AA in said pharmaceutical composition may vary between 10:90 and 90:10 is preferably 20 to 80. Since OVT enhances the activity of AA and AA has more specificity than OVT, the combination of OVT and AA exhibits both enhanced activity and specificity towards cancer cells.

In a still further embodiment, the pharmaceutical composition will comprise OVT or OVT related substances in combination with at least one compound of following Formula II or a pharmaceutically acceptable salt thereof

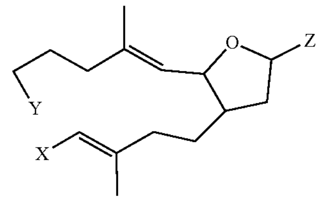

wherein

- X represents an alkyl, alkylene, alkenyl, alkenylene, alkynyl or alkynylene group, optionally having, at least, one substituent selected from the group of —$OR^1$ and —$NR^1R^2$;
- Y represents —OTBS, —$OR^1$, —$NR^1R^2$;
- Z represents —$OR^3$; and
- $R^1$, $R^2$, and $R^3$ each independently stands for H, alkyl, alkenyl, alkynyl, aryl, heteroaryl, or heterocyclyl.

Compounds of formula II are known from WO2016/027005 for use in treatment of Human Papillomavirus induced carcinoma. Preferred compounds of formula II include for example the following:

5-[(E)-5-[tert-butyl(dimethyl)silyl]oxy-2-methyl-pent-1-enyl]-4-[(3E)-3-methylhexa-3,5-dienyl]tetrahydrofuran-2-ol;

tert-butyl-[(E)-5-[5-methoxy-3-[(3E)-3-methylhexa-3,5-dienyl]tetrahydrofuran-2-yl]-4-methyl-pent-4-enoxy]-dimethyl-silane; and (E)-6-[2-[(E)-5-[tert-butyl(dimethyl)silyl]oxy-2-methyl-pent-1-enyl]-5-methoxy-tetrahydrofuran-3-yl]-4-methyl-hex-3-en-1-ol.

In a still further embodiment, the pharmaceutical composition will comprise OVT or OVT related substances in combination with Anisomelic acid or pharmaceutically acceptable salts thereof and at least one compound of Formula II or a pharmaceutically acceptable salt thereof.

In another embodiment, the pharmaceutical composition will comprise Ovatodiolide or Ovatodiolide OVT related substances in combination with Anisomelic acid or pharmaceutically acceptable salts thereof, together with at least one approved cancer therapeutic.

In a still further embodiment, the pharmaceutical composition will comprise a therapeutically effective amount of an enriched extract from *Anisomeles malabarica, A. indica* or *A. ovata*, wherein said extract comprises Ovatodiolide or Ovatodiolide related substances and AA.

In an embodiment, the combined amount of OVT and AA in the enriched extract is at least 5% by weight, such as 5 to 30% by weight, preferably at least 10%, at least 15%, or above by weight, more preferably about 20% or above by weight, based on the weight % of the dry material of the enriched extract.

In a further embodiment, the amount of OVT in the enriched extract is at least 10% by weight, preferably at least 13%, more preferably at least 15%, and the amount of AA is at least 8% by weight, preferably at least 10% by weight, based on the weight % of the dry material of the enriched extract.

In an embodiment, a process for the preparation of an enriched extract comprising Ovatodiolide or Ovatodiolide related substances and AA comprises the step of extracting *Anisomeles malabarica, A. indica* or *A. ovata* plant material with an aqueous alcoholic or ether solvent. Examples of suitable aqueous alcoholic solvents include but are not limited to lower alcohols, in particular alcohols having 1 to 6 carbon atoms, such as ethanol, methanol, propanol, isopropanol, and butanol, particularly ethanol or isopropanol, preferably isopropanol. Examples of preferred ether (or ester) solvents include but are not limited to methyl tert-butyl ether and ethyl acetate, particularly methyl tert-butyl ether.

In a further embodiment, extraction of *Anisomeles malabarica, A. indica* or *A. ovata* plant material is performed in the presence of activated carbon or the extract obtained from the extraction of plant material is treated with activated carbon. When the extract is treated with activated carbon, activated carbon is added to the extract and the mixture is stirred for a period of time, for example for 1 to 72 h, for example 2 to 48 h, in particular 10 to 30 h, or for approximately 24 h. After that period of time, the mixture is filtered. Alternatively, the extraction can be performed in the presence of activated carbon, for example by soaking the plant material and the activated carbon in an extraction solvent for an appropriate period of time, for example for 1 to 72 h, for example 2 to 48 h, in particular 10 to 30 h, or for approximately such as 24 h. After that period of time, the mixture is filtered. By using activated carbon, in combination of suitable solvents, it is possible to recover mostly hydrophobic compounds (such as AA and OVT) in the extract, as the activated carbon removes most of the hydrophilic compounds.

In an embodiment, the amount of activated carbon is 1 to 30%, for example 5-15% of the weight of the plant material, typically about 10% of the weight of the plant material.

After removing the solvent, an extract is obtained, which after washing and optional further concentration provides an enriched extract comprising OVT and AA. The method of the invention provides enriched extracts wherein the yield of the active components Ovatodiolide or Ovatodiolide related substances and AA is high and which can be used without further purification in various pharmaceutical products, particularly in products for treatment of warts.

In one embodiment, the yield of Ovatodiolide or Ovatodiolide related substances and AA is at least 25%, in particular 30 to 99%, for example 40 to 98%, calculated from the weight of OVT or OVT related substances and AA present in the starting materials.

The pharmaceutical compositions can be in any suitable form. Typical pharmaceutical forms include aqueous, oleaginous suspension, dispersions as well as sterile powders, which may be used for the extemporaneous preparation of injectable solutions or dispersions. It can be used for topical (e.g. intravaginal) application, for example in the form of intravaginal creams or by application of prolonged release solid preparations, such as sustained release pharmaceutical plasters. The compositions may also be solutions or suspensions in non-toxic diluents or solvents, e.g. as solutions in 1,3-butanediol. Alternatively, they can be prepared as micro-emulsions and administered, for example orally.

In an embodiment, the pharmaceutical compositions comprising enriched extracts of *A. malabarica* and/or *A. indica* are in the form of pharmaceutical formulations comprising one or more pharmaceutically acceptable excipients or carriers for parenteral, oral, or topical treatment, particularly for topical treatment as an ointment, cream, gel, aerosol, powder, oil, or as suppositories, eye, nose or ear drops.

In a further embodiment, the pharmaceutical compositions comprising enriched extracts of *A. malabarica* and/or *A. indica* are in the form of oil or oil-in-water topical pharmaceutical formulations for the treatment of papillomavirus associated diseases of the skin or mucosa of a mammal.

The carrier can be a solvent or dispersion medium containing, for example, water, polyol (for example, glycerol, propylene glycol, and liquid polyethylene glycol, and the like), ethanol, and mixtures of the indicated components, various vegetable oils, Ringer's solution, and isotonic sodium chloride solutions. In addition, fixed oils may be employed as a solvent or suspending medium. Fixed oils that can be employed include synthetic mono- or diglycerides. Further, fatty acids such as oleic acid find use in the preparation of injectables.

The pharmaceutical compositions of the present invention may also comprise nanoparticles or nanocarriers. Nanoparticles or nanocarriers include for example polymeric nanoparticles (PNPs), magnetic nanoparticles, nanoparticles based on solid lipids, silver and gold nanoparticles, dendrimer based nanocarriers, supramolecular nanocarriers, and carbon nanocarriers, such as carbon nanotubes. Traditional nanocarriers for delivery of chemotherapeutic drugs include nanocarriers based on liposomes or micelles. Thus, in one embodiment, cells were treated with OVT loaded into Folic acid (FA) conjugated polyethyleneimine (PEI)/chitosan coated nanoparticles/nanorods.

As conventional, the pharmaceutical composition may contain formulation materials for modifying, maintaining or preserving, for example, the pH, osmolarity, viscosity, clarity, color, isotonicity, odor, sterility, stability, the rate of dissolution or release, adsorption or penetration of the composition.

The pharmaceutical compositions can also be selected for inhalation or for delivery through the digestive tract, such as orally. The preparation of such pharmaceutically acceptable compositions is within the skill of the art. OVT can be present in the same pharmaceutical composition. They can also be comprised in different pharmaceutical compositions which are, for example, supplied in the same package.

Although the above description primarily relates to human objects, pharmaceutical compositions for veterinary use are also included herein. Particularly, pharmaceutical compositions for veterinary use in anti-papillomavirus treatment of non-human mammals, for example bovines, are included herein. Thus, in one embodiment the present invention provides for a pharmaceutical composition for treatment or prevention Bovine papillomavirus (BPV) mediated cancers or BPV associated non-cancerous lesions, like warts, in bovine. In a further embodiment, the present invention provides for a pharmaceutical composition for treatment or prevention of animal papillomavirus mediated cancers or papillomavirus associated non-cancerous lesions, like warts, in other non-human mammals, for example rabbits, or rodents such as hamsters, mice and companion animals such as dogs, cats, horses etc.

Particularly, the topical formulations of the present invention, such as the pharmaceutical compositions comprising the enriched extracts of the invention, find use in human or veterinary use in the form of creams, ointments, gels, aerosols, powders, or oils, particularly in the form of creams, gels or ointments for the treatment of animal papillomavirus mediated cancer or animal papillomavirus associated non-cancerous lesions, such as warts.

The following non-limiting examples illustrate embodiments of the invention.

Experimental

The experimental results presented below demonstrate that OVT, in particular Ovatodiolide, depletes the viral oncoproteins E6/E7 and cellular inhibitor of apoptosis protein 2 (cIAP2), thus inducing apoptosis in SiHa HPV16 positive cervical cancer cells.

The results show that OVT induced apoptosis more efficiently than AA in cervical cancer cells. The potency of OVT was shown to be considerably higher than that of AA in all experiments.

Materials and Methods

OVT (in this case Ovatodiolide) was isolated from *Anisomeles malabarica* as previously described by Arisawa et al., 1986 with few modifications. A 100 mM stock solution was prepared in DMSO at room temperature.

SiHa and HeLa cervical cancer cells and Human Dermal Fibroblasts (HDF) were cultured in DMEM (Sigma-Aldrich, St Louis, MO, USA). The medium was supplemented with 10% fetal calf serum (BioClear, Wiltshire, UK), 2 mM L-glutamin, 100 U/ml penicillin, 100 μg/ml streptomycin (Sigma-Aldrich).

Assessment of Cytotoxicity of OVT

MTT Assay:

The MTT assay is a colorimetric assay widely used to study cell viability. It is based on the ability of NAD(P)H-dependent cellular oxidoreductase enzymes to reduce the MTT tetrazolium dye. The cells were treated with 0, 5, 10, 20 & 40 μM of OVT & AA for 72 h and then MTT was added and cytotoxicity was analyzed by a plate reader.

High Content Imaging:

The Cell-IQ Real-time imaging provides information on how the compounds are affecting cell morphology and cell proliferation at various doses up to 72 h. A rigorous image analysis protocol was developed to assess the effects of the compounds on cell proliferation.

Assessment of Cell Death

SiHa cells were treated with 0, 20 & 40 μM AA or OVT or solvent control for 24 & 48 h. Activated caspase-3 in cells was labeled with phyco-erythrin-conjugated antibody according to manufacturer's protocol (PE Active Caspase-3 Apoptosis Kit; BD Pharmingen, San Diego, CA) and analyzed by FACSCalibur flow cytometer (FL-2, FSC, BD Pharmingen).

In Vitro p53 Degradation Assay

The plasmids used in the in vitro translation assay, full length, p2207 pGEM p53 was a gift from Peter Howley (Addgene plasmid #1-853) and human papillomavirus type 16 E6 (MBP-E6), was a gift from Gilles Trave. Each protein was translated in separate reactions using the protocol provided in the TNT T7 coupled rabbit reticulocyte lysate systems (Promega). For p53 degradation assay, the translation reactions were combined in the absence or presence of the respective extracts at the indicated concentrations or a DMSO control. Following incubation, reactions were analyzed on SDS-PAGE followed by p53 Western blotting.

Western Blotting

Whole cell lysates were prepared by lysing the cells in Laemmli sample buffer (Laemmli, 1970) and boiling the samples for 10 min after which proteins were separated in 12.5-15% SDS-PAGE. Western blotting was performed using antibodies against caspase 3 (Cell Signaling), HPV16 E6, E7 (Santa Cruz Biotechnology, Inc, Santa Cruz, CA), and β-actin (clone AC-40; Sigma-Aldrich). Horseradish peroxidase-conjugated secondary antibodies were obtained from Southern Biotechnology Associates (Birmingham, AL), Promega (Madison, WI) and Amersham Biosciences (Freiburg, Germany). The results were visualized using the ECL method (Amersham Biosciences) on X-ray film. The presented Western blot results are representative of at least three independent experiments.

The onco-E6 assay is a kit and was performed according to the manufacturer's instructions (Arbor Vita Corporation).

Skin irritation tests in rabbits and acute oral toxicity tests in rats were performed according to the OECD guidelines.

Results

HPV-positive cervical cancer cells, SiHa, Hela cells, patient-derived HPV positive head and neck cancer cells and non-cancer human fibroblasts were treated with OVT at the dose range of 0, 5, 10, 20 and 40 μM and subjected to MTT assay and $IC_{50}$ values were determined. Table 1 shows the IC50 value of OVT in various cell lines.

Figure 1B:
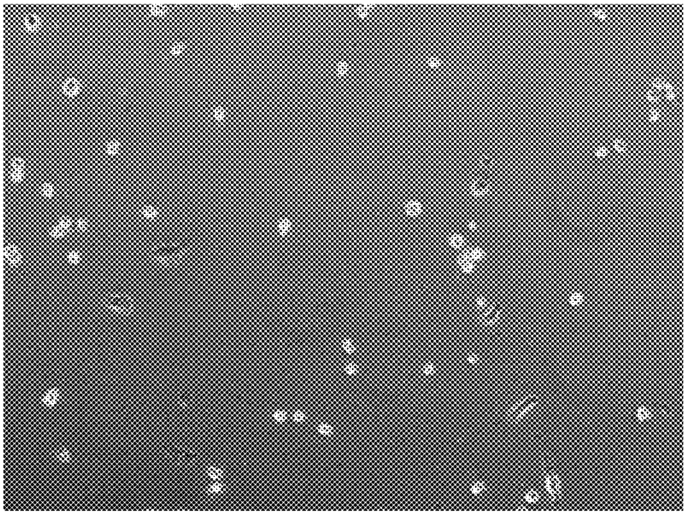

OVT would induce apoptotic death of cultured SiHa cervical cancer cells. Representative phase contrast images of untreated and OVT-treated cells are shown in FIGS. 1A and 1B respectively. As seen from the images, OVT induced cell death in SiHa cells at 40 μM (FIG. 1*i*).

Figure 2A:
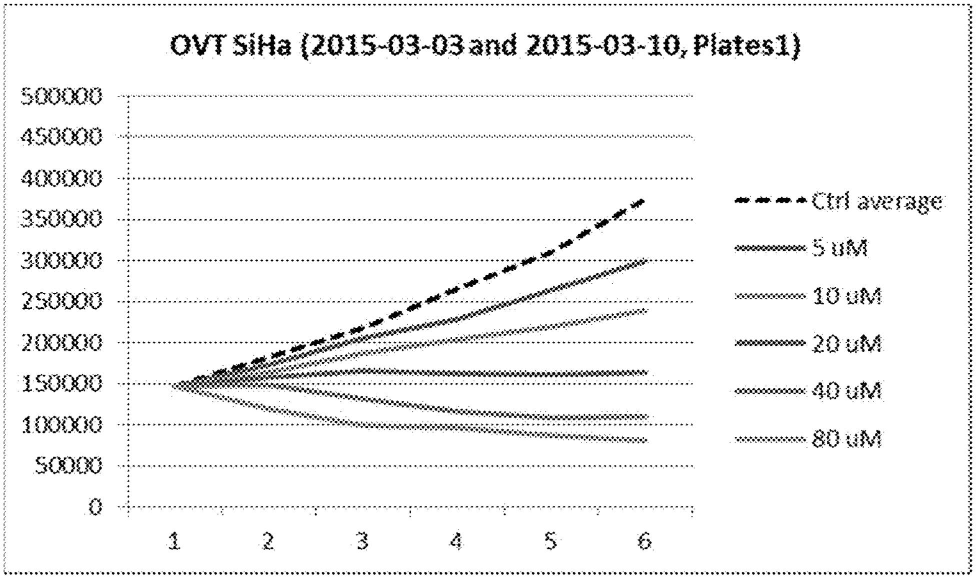
FIG. 2 demonstrates that OVT reduces cell growth in cervical cancer cell lines SiHa (FIG. 2A) and HeLa (FIG. 2B). SiHa cells—HPV 16 positive cervical cancer cell line; HeLa—HPV 18 positive cervical cancer cell line. Cell proliferation of SiHa and HeLa cervical cancer cell lines was observed for a total of 72 hours with increasing doses of OVT. Numbers 1-6 on the x-axis indicate 12 h intervals. The area of the plate that cells cover is indicated on the y-axis (arbitrary number of units).
Figure 2B:
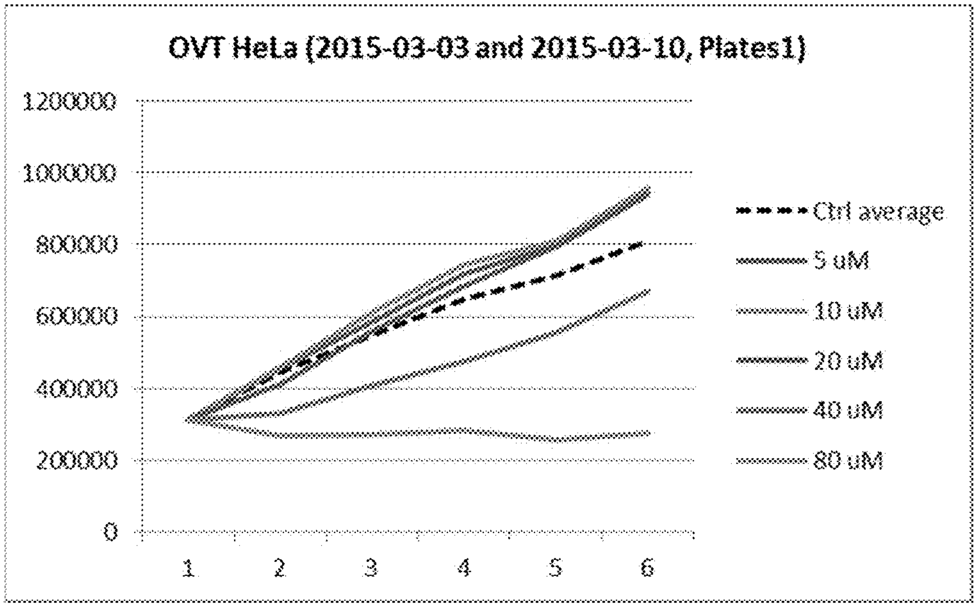

The cells were imaged by high content imaging in Cell-IQ and the proliferation of the cells was observed till 72 h. The graph (FIGS. 2A & B) shows that OVT inhibited the cell proliferation both in SiHa & HeLa cells effectively at various doses.

Figure 3A:
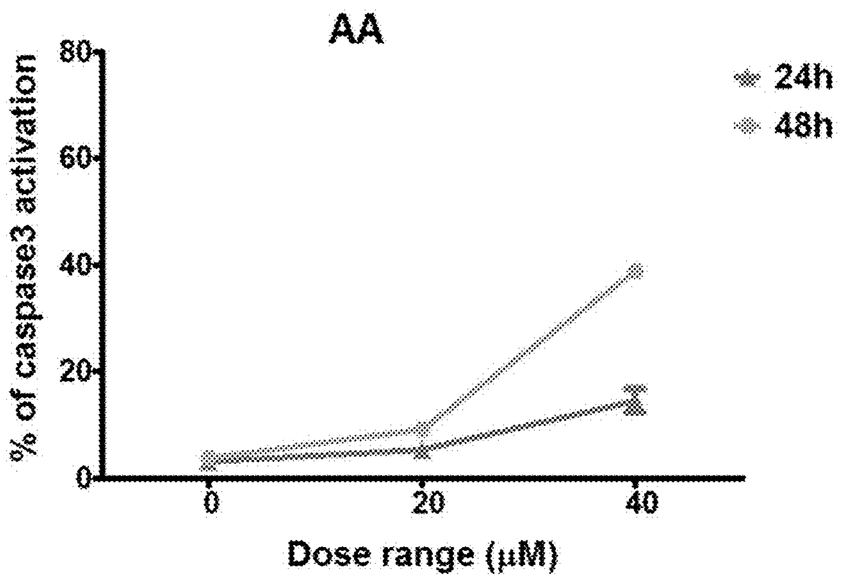
FIG. 3A shows the caspase-3 activation by Anisomelic acid (AA) at an increasing dose range.
Figure 3B:
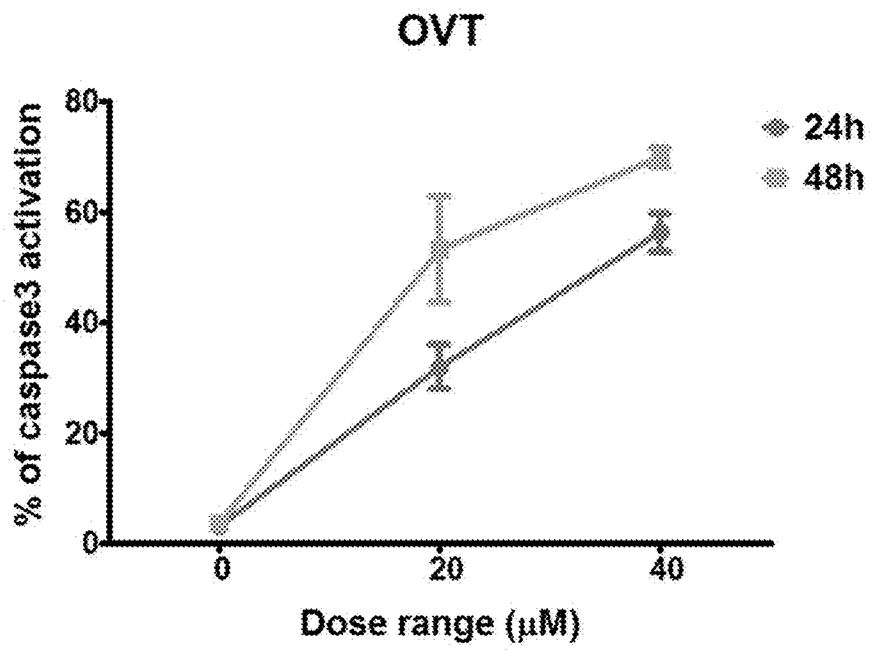
FIG. 3B shows the caspase-3 activation by Ovatodiolide (OVT) at an increasing dose range. OVT is more effective than AA in inducing caspase-3 activation which is a hallmark of apoptosis.
Figure 4:
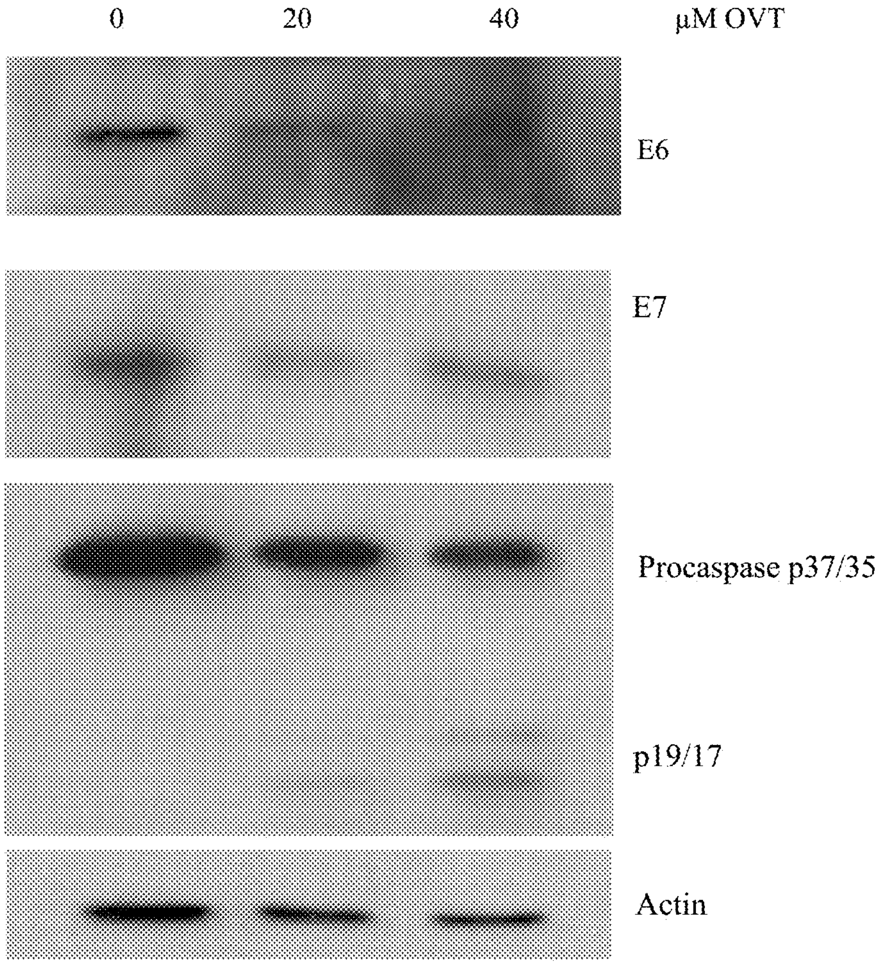
FIG. 4 shows Western blot analysis of the effect of OVT on SiHa cells. OVT induced downregulation of the HPV E6 and E7 viral proteins.

We then incubated the cells with 0, 20 & 40 μM AA & OVT 24 and 48 hours, and determined the percentage of cells that contained activated caspase-3 as a measure of apoptosis. A marked activation of caspase-3 was observed after 48 h at 40 μM AA (FIG. 3A). However, a higher activation of caspase-3 was found already at 20 μM OVT after 24 h (FIG. 3B). OVT almost doubled the activation of caspase-3 compared to the activation achieved by AA at the same concentration (40 μM) after 48 h.

SiHa cervical cancer cells have been transformed by high-risk human papillomavirus (HPV). As E6 and E7 play such critical roles in SiHa cell transformation, the expression of these viral proteins was examined. Treatment with 20-40 μM OVT also induced the cleavage of caspase-3 thus demonstrating that OVT is capable of effectively inducing degradation of E6 and E7 viral proteins leading to cell death.

Figure 5:
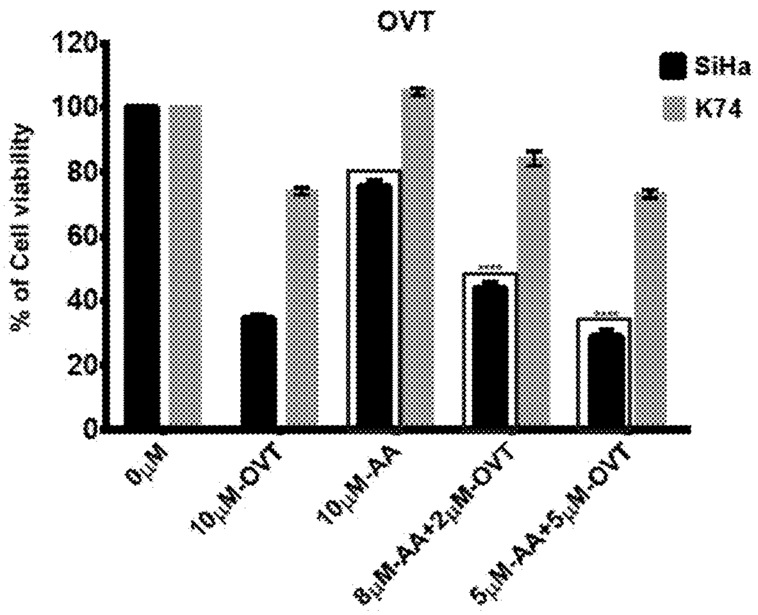
FIG. 5 demonstrates that the combination of AA and OVT leads to significantly enhanced cell death in SiHa cells when compared to AA alone. The combination does not induce cell death in the primary cells (K74) as effectively as in the SiHa cells, thus showing a higher specificity.
Figure 6:
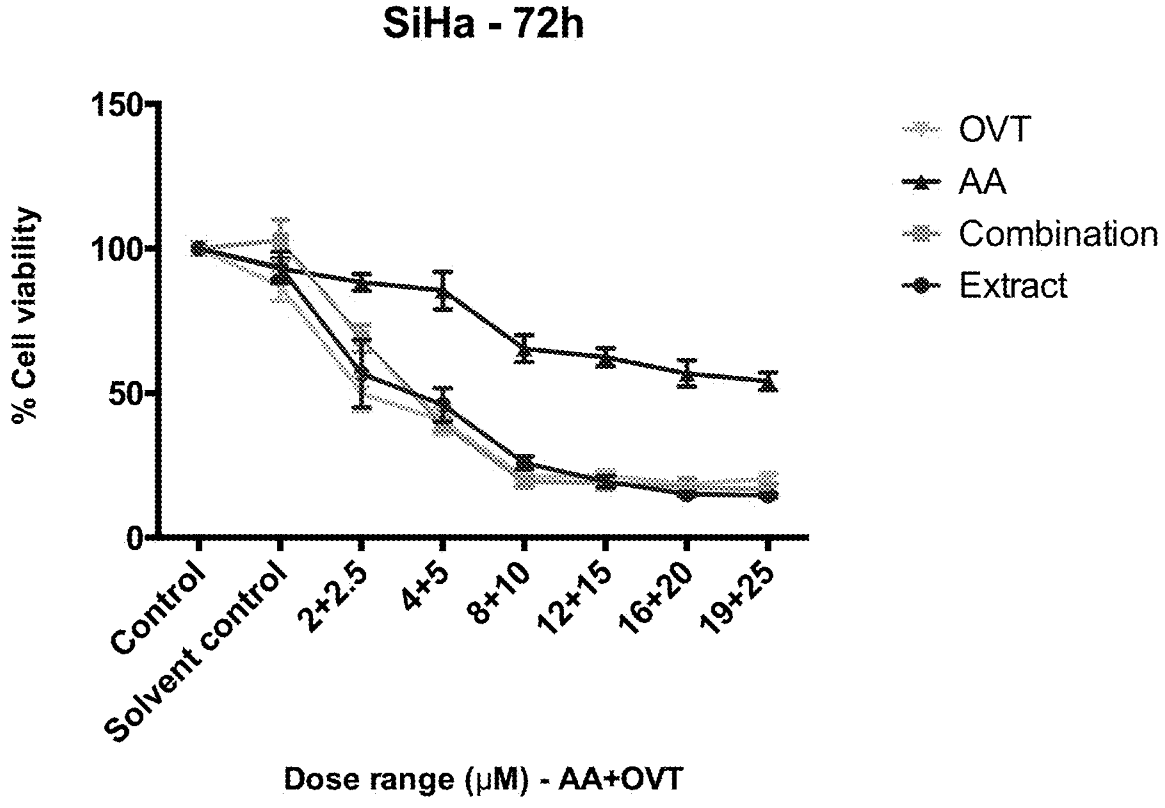
FIG. 6 illustrates cell viability values (MTT assay) and demonstrates that the extract comprising approximately 16% OVT and 13% AA effectively reduced cell viability at a dose dependent manner. SiHa cells were treated with AA, OVT, or their combination along with the extracts for 72 h (2, 4, 8, 12, 16, 19 μM AA and 2.5, 5, 10, 15, 20, 25 μM OVT).
Figure 7:
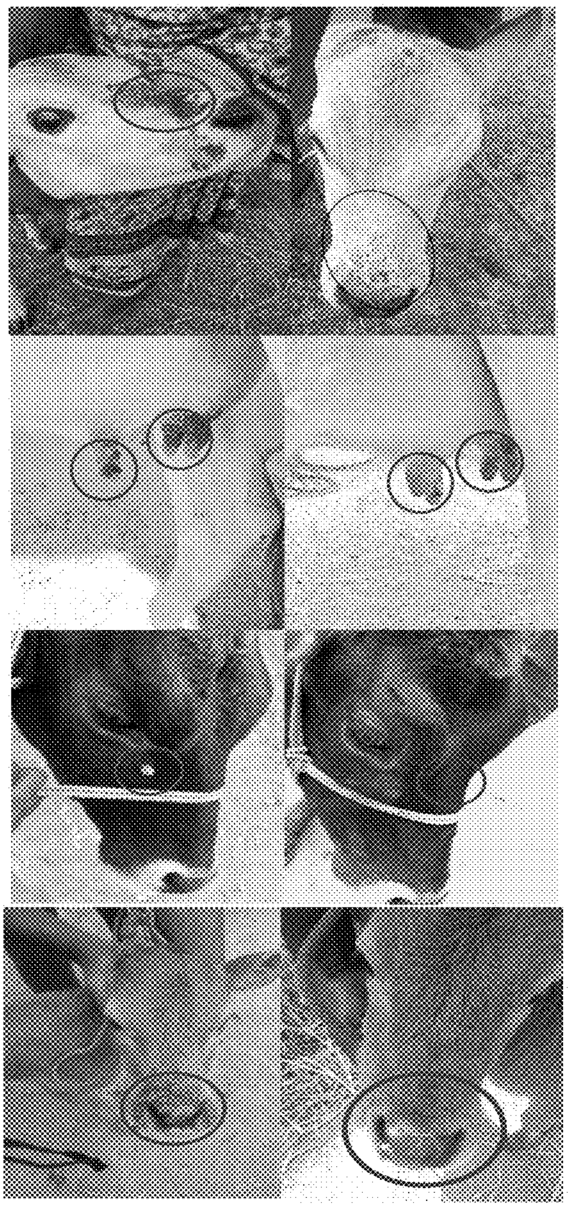
FIG. 7 shows the effect of a topical gel/cream containing the enriched/refined extracts of *Anisomeles malabarica* and/or *Anisomeles indica* on cattle warts. The warts were totally removed after treatment in a span of 5-10 days.
Figure 8:
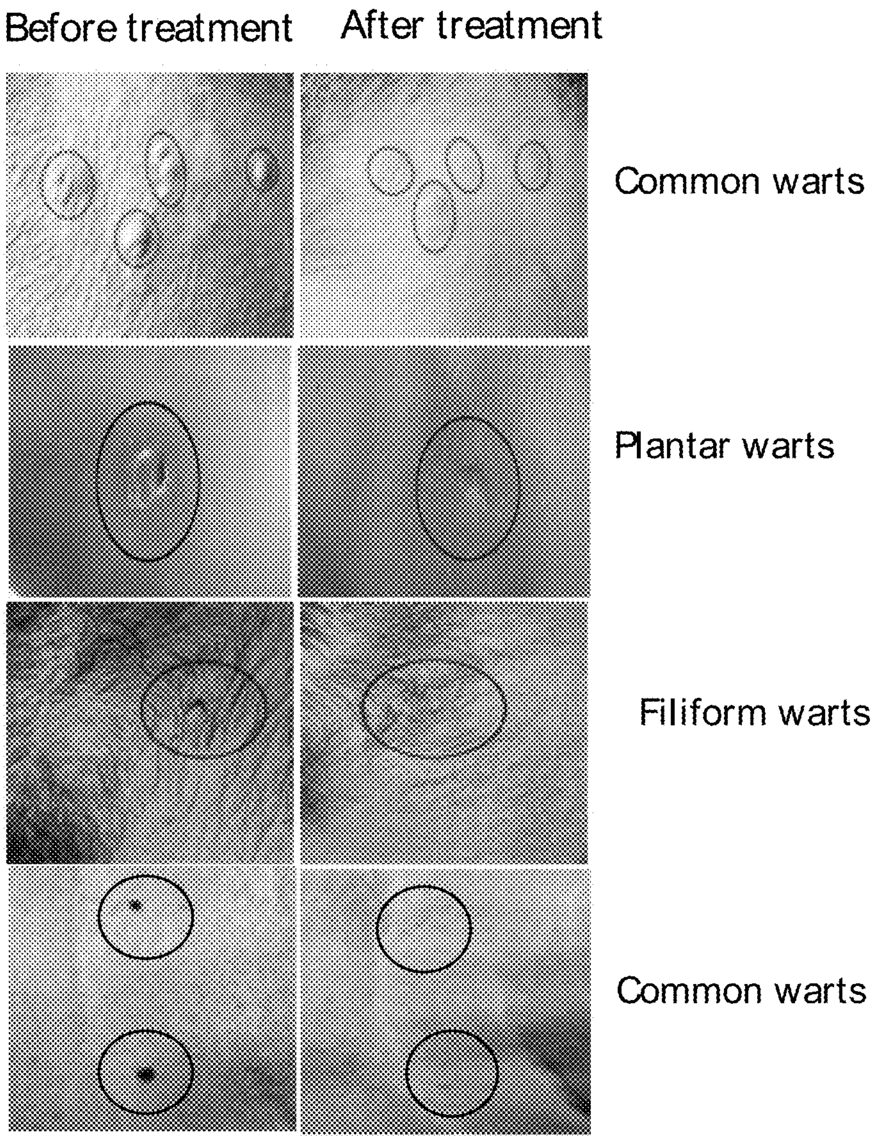
FIG. 8 shows the effect of a topical gel/cream containing the enriched/refined extracts of *Anisomeles malabarica* and/or *Anisomeles indica* on human volunteer warts. The warts disappeared after treatment. The treatment duration ranged from 3 to 10 days.
Figure 9A:
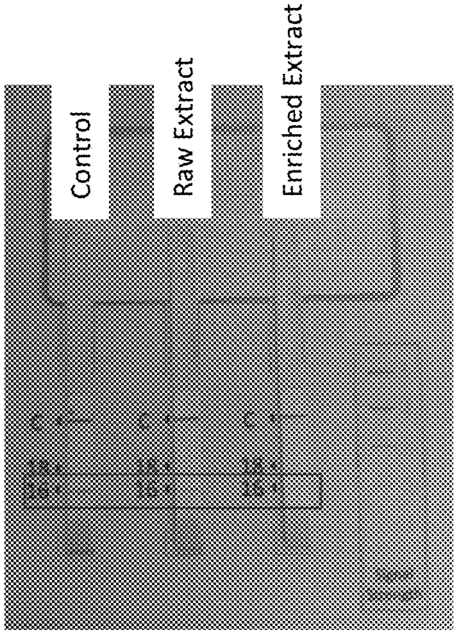
FIG. 9A shows the downregulation of E6 protein using onco-E6 assay, upon treatment with the raw extract and enriched extract.
Figure 9B:
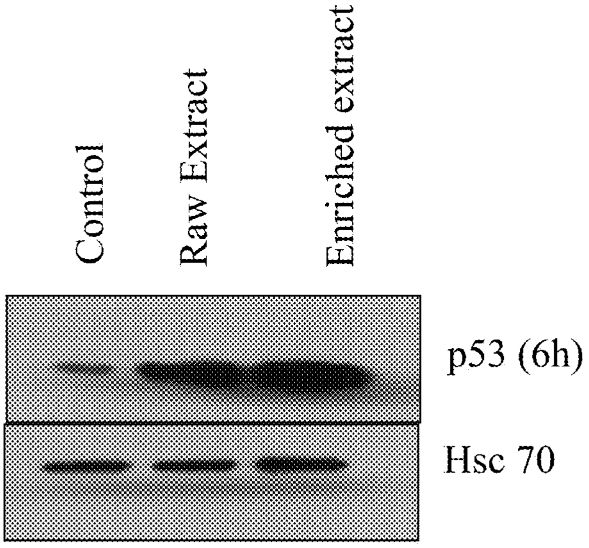
FIG. 9B shows the representative western blots of p53 in the p53 degradation reaction treated with the raw extract and enriched extract. The gels were run separately and reprobed with Hsc70 as loading control.
Figure 10:
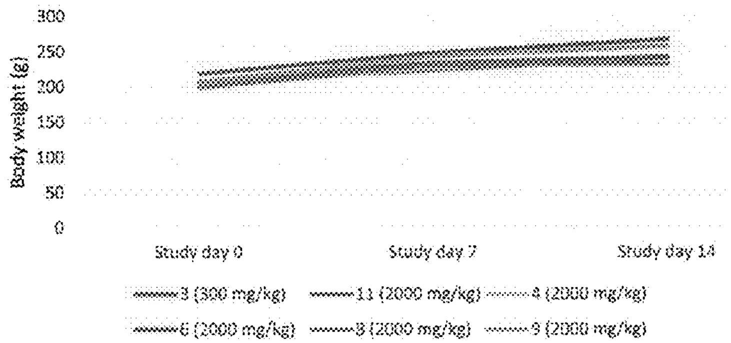
FIG. 10 shows the acute oral toxicity tests done on rats with the enriched extracts.

AA and OVT have been tested in SiHa and K74 cells for their synergistic action and FIG. 5 shows that OVT increases the efficacy of AA especially in the combination of (8 μM AA+2 μM OVT) at the same time being nontoxic to K74 primary fibroblast cells, thus showing that even low amounts of OVT in combination with other drugs can make them more effective and at the same time less toxic.

We tested the cream in few cow warts in India with the help of veterinary doctors and the results show that the warts are cleared and are removed effectively with no or little side effects. In addition, few volunteers who already tested the cream on their warts had positive experience as the cream removed the warts.

We assessed the E6 protein expression by onco-E6 assay. We treated the SiHa cells with a raw extract and enriched extract and observed that E6 protein was down regulated after treatment with the extracts. The concentrations of AA and OVT in the extracts were approximately 12% AA, 8% OVT in the raw extract and 16% AA and 9.8% OVT in the enriched extract.

TABLE 1

MTT assay, $IC_{50}$ (μM)

| | | | Patient derived HPV positive Head and Neck cancer cells | | | | | Primary skin fibroblast cells | |
|---|---|---|---|---|---|---|---|---|---|
| Compounds | HPV 16 SiHa | HPV 18 HeLa | UT-SCC 60A | UT-SCC 60B | UT-SCC 65 | UT-SCC 69 | UT-SCC 102 | K87 | K74 |
| Anisomelic acid (AA) | 32.08 | 33.25 | 17.96 | 22.82 | 42.79 | 23.94 | 28.18 | — | — |
| Ovatodiolide | 10.67 | 10.67 | 5.533 | 3.332 | 14.08 | 0.859 | 7.731 | 19.67 | 13.24 |

It is seen that OVT is highly toxic to HPV positive cells compared to the non-cancer human fibroblasts whereas AA is not toxic at all to non-cancer human fibroblast cells. This shows that OVT has better efficacy compared to AA whereas AA has more specificity compared to OVT at 72 h.

In order to examine the mechanism underlying the previously reported cytotoxicity of OVT, we investigated if We also tested the raw and enriched extract in the p53 degradation assay and we found that the extracts inhibited degradation of p53 by E6 T in the in vitro translation assay.

We also analyzed the skin irritation and oral toxicity of the extracts and found them to be non-toxic. Dermal application of the enriched extract to female New Zealand White Rabbits did not result in mortality or any abnormal clinical sign throughout the study period. There were no test item related effects on body weight. The average dermal scoring (of 24 h, 48 h and 72 h) of each of three animals was 0.00. The pH of the test item was measured with 1% (w/v) formulation in Milli Q water and it was 4.67, which was between 2 to 11.5, an acceptable limit. Hence, it was concluded that the enriched extract was "Non Irritant" when applied dermally to female New Zealand White Rabbits and the extract can be classified in "No Category" according to GHS.

We did acute oral toxicity test to investigate the acute toxicity of our refined extract after a single oral administration in the rat. The study provided information on the major toxic effects of the test item on possible target organs. As the dose 300 mg/kg was not toxic, we did the study in a higher dose of 2000 mg/kg and the results showed that the extract did not show any sign of toxicity in the rats after a single oral administration. There were no abnormalities recorded at necropsy.

Preparation of an Extract Comprising AA and OVT

*Anisomeles malabarica* plant material was extracted with ethanol and the extract was concentrated to dryness. The residue extract was dissolved in chloroform and filtrated through a pad of celite. The filtrate was concentrated to dryness and dissolved in methanol. The methanol solution was washed with hexane and then concentrated to dryness to give dark green viscose oil, which contains approximately 16 weight % of OVT and approximately 13 weight % of AA.

As apparent from the above, the combined content of OVT and AA in the enriched extract was approximately 29%. The enriched extract also contained i.a. the following approximate amounts:

5% of fatty acids;
4% of fats and lipids;
2% of sterols;
2% of heavy alkanes;
2% of known diterpenes.

The enriched extract may also contain up to about 5% of other cembranolides (AA and OVT derivatives).

Comparison of Solvents in the Preparation the Enriched Extract

*Anisomeles malabarica* plant material was extracted with number of different solvents. The results are presented in Table 2:

TABLE 2

Extraction of *Anisomeles malabarica* with different solvents

| Solvent | Weight % of extractives | % of OVT/AA |
|---|---|---|
| 95% Ethanol (5% water) | 22% | 3/5 |
| Methanol | 22% | 4/6 |
| MTBE | 9% | 9/13 |
| 2-propanol | 12% | 8/12 |
| EtOAc | 8% | 7/12 |

The plant material was soaked in the solvent for 24 h (mixing with magnetic stirrer), followed by filtration and concentration to dryness. The amount of extract was gravimetrically determined and the concentration of AA+OVT was determined by quantitative GC.

Optimized Procedure for Preparation of the Enriched Extract

Leafs from *Anisomeles malabarica* were stirred for 24 h with 2-propanol or MTBE, then activated carbon (10% based on the plant material) was added and the mixture was stirred for additional 24 h. Then the mixture was filtered and the solvent removed.

Alternatively, the extraction was performed in the presence of activated charcoal (10% of activated charcoal compared to weight of the plant material). As a result, 9% extractives were obtained as yellow oil (content of OVT/AA, %—10/16).

For further enrichment of the extract, the residue was dissolved in methanol and extracted with n-hexane to give yellow solid after solvent removal (8% of the plant material, content of OVT/AA, %—12/18).

Preparation of a Topical Gel/Cream of Enriched Extract

For preparation of gel, 1-2% of Carbopol 940 or Carbopol 934 was finely dispersed in 50:50 propylene glycol:water mixture and stirred continuously at 400 rpm for 2 hrs. Then, the enriched extract (10 to 30%) of *Anisomeles malabarica* and/or *Anisomeles indica* was dissolved in 10-15% of ethanol and 20% of glycerol mixture. The dissolved extract solution is then added to the Carbopol mixture and mixed overnight. The pH of the gel was adjusted to 6 by the addition of triethanolamine. The overall percentage/weight of the gel was adjusted with propylene glycol:water mixture.

REFERENCES

Arisawa, M. et al., 1986. "Biological active macrocyclic diterpenoids from Chinese drug "Fáng Féng Cáo"; II. Derivatives of ovatodiolids and their cytotoxicity". *Planta medica*, (4), p. 297-299.

Jarrett W F H, McNeil P E, Grishaw W T R, Selan I E and McIntyre W I M (1978). "High incidence area of cattle cancer with a possible interaction between an environmental carcinogen and a papillomavirus". *Nature,* 274, p. 215-217.

Scudellari M., 2013. "HPV: Sex, Cancer, and a Virus". *Nature.* 503(7476), p. 330-332.

Zur Hausen 1-1(1978). "Condyloma acuminata and human genital cancer". *Cancer Research,* 36, p. 794.

The invention claimed is:

1. A method of treating or preventing a papillomavirus-mediated cancer in a mammal, the method comprising:

administering a therapeutically effective amount of ovatodiolide, isoovatodiolide, 4,5-epoxovatodiolide, 4-hydroxy-5-enovatodiolide, 4-methylene-5-hydroxyovatodiolide, or 4-methylene-5-oxovatodiolide, or an optical isomer, or a pharmaceutically acceptable salt thereof to said mammal, wherein the administering inhibits E6 and E7 expression in said mammal, and wherein no therapeutically effective amount of anisomelic acid or a pharmaceutically acceptable salt thereof is administered to the mammal.

2. The method according to claim 1, wherein the papillomavirus-mediated cancer comprises cervical cancer, an oropharyngeal cancer, or head and neck cancer.

3. The method according to claim 2, wherein the papillomavirus-mediated cancer comprises cervical cancer.

4. The method according to claim 1, wherein the ovatodiolide, isoovatodiolide, 4,5-epoxovatodiolide, 4-hydroxy-5-enovatodiolide, 4-methylene-5-hydroxyovatodiolide, or 4-methylene-5-oxovatodiolide, or the optical isomer, or the pharmaceutically acceptable salt thereof is administered to the mammal in a dosage of 5 mg/kg to about 1000 mg/kg body weight.

5. The method according to claim 1, further comprising administering a therapeutically effective amount of an additional cancer therapeutic to the mammal.

6. The method according to claim 1, wherein the administering is done topically.

7. A method of treating or preventing papillomavirus-mediated genital or non-genital warts in a mammal, the method comprising:

administering a therapeutically effective amount of ovatodiolide, isoovatodiolide, 4,5-epoxovatodiolide, 4-hydroxy-5-enovatodiolide, 4-methylene-5-hydroxyovatodiolide, or 4-methylene-5-oxovatodiolide, or an optical isomer, or a pharmaceutically acceptable salt thereof to said mammal.

8. The method of claim 7, wherein the method treats or prevents papillomavirus-mediated genital warts.

9. The method according to claim 7, wherein the administering is done topically.

10. The method according to claim 7, wherein the ovatodiolide, isoovatodiolide, 4,5-epoxovatodiolide, 4-hydroxy-5-enovatodiolide, 4-methylene-5-hydroxyovatodiolide, or 4-methylene-5-oxovatodiolide, or the optical isomer, or the pharmaceutically acceptable salt thereof is administered to the mammal in a dosage of 0.001 mg/kg to about 1000 mg/kg body weight.

11. The method according to claim 7, further comprising administering a therapeutically effective amount of anisomelic acid or a pharmaceutically acceptable salt thereof to the mammal.

12. The method according to claim 11, wherein the ovatodiolide, isoovatodiolide, 4,5-epoxovatodiolide, 4-hydroxy-5-enovatodiolide, 4-methylene-5-hydroxyovatodiolide, or 4-methylene-5-oxovatodiolide, or the optical isomer, or the pharmaceutically acceptable salt thereof and the anisomelic acid or the pharmaceutically acceptable salt thereof are administered in a pharmaceutical composition, and wherein the weight ratio of the ovatodiolide, isoovatodiolide, 4,5-epoxovatodiolide, 4-hydroxy-5-enovatodiolide, 4-methylene-5-hydroxyovatodiolide, or 4-methylene-5-oxovatodiolide, or the optical isomer, or the pharmaceutically acceptable salt thereof to the anisomelic acid or the pharmaceutically acceptable salt thereof in said pharmaceutical composition is between 10:90 and 90:10.

13. The method according to claim 11, wherein the ovatodiolide, isoovatodiolide, 4,5-epoxovatodiolide, 4-hydroxy-5-enovatodiolide, 4-methylene-5-hydroxyovatodiolide, or 4-methylene-5-oxovatodiolide, or the optical isomer, or the pharmaceutically acceptable salt thereof and the anisomelic acid or the pharmaceutically acceptable salt thereof are administered in a pharmaceutical composition, and wherein the therapeutically effective amount of the ovatodiolide, isoovatodiolide, 4,5-epoxovatodiolide, 4-hydroxy-5-enovatodiolide, 4-methylene-5-hydroxyovatodiolide, or 4-methylene-5-oxovatodiolide, or the optical isomer, or the pharmaceutically acceptable salt thereof is at least 10 wt % and the therapeutically effective amount of the anisomelic acid or the pharmaceutically acceptable salt thereof in the pharmaceutical composition is at least 8 wt %.

14. The method according to claim 11, wherein the ovatodiolide, isoovatodiolide, 4,5-epoxovatodiolide, 4-hydroxy-5-enovatodiolide, 4-methylene-5-hydroxyovatodiolide, or 4-methylene-5-oxovatodiolide, or the optical isomer, or the pharmaceutically acceptable salt thereof and the anisomelic acid or the pharmaceutically acceptable salt thereof are administered in a pharmaceutical composition, and wherein the combined amount of the ovatodiolide, isoovatodiolide, 4,5-epoxovatodiolide, 4-hydroxy-5-enovatodiolide, 4-methylene-5-hydroxyovatodiolide, or 4-methylene-5-oxovatodiolide, or the optical isomer, or the pharmaceutically acceptable salt thereof and the anisomelic acid or the pharmaceutically acceptable salt thereof in the pharmaceutical composition is from 5 to 30 wt %, based on the wt % of the dry material of the pharmaceutical composition.

15. The method according to claim 1, wherein a therapeutically effective amount of ovatodiolide is administered to the mammal.

16. The method according to claim 7, wherein a therapeutically effective amount of ovatodiolide is administered to the mammal.

17. The method of claim 7, wherein the ovatodiolide, isoovatodiolide, 4,5-epoxovatodiolide, 4-hydroxy-5-enovatodiolide, 4-methylene-5-hydroxyovatodiolide, or 4-methylene-5-oxovatodiolide, or an optical isomer, or a pharmaceutically acceptable salt thereof is the sole therapeutic agent delivered to said mammal.

18. The method according to claim 7, wherein the ovatodiolide, isoovatodiolide, 4,5-epoxovatodiolide, 4-hydroxy-5-enovatodiolide, 4-methylene-5-hydroxyovatodiolide, or 4-methylene-5-oxovatodiolide, or the optical isomer, or the pharmaceutically acceptable salt thereof is administered to the mammal in a dosage of 5 mg/kg to about 1000 mg/kg body weight.

* * * * *